United States Patent [19]

Snyder et al.

[11] Patent Number: 5,130,001

[45] Date of Patent: Jul. 14, 1992

[54] URANIUM ISOTOPE SEPARATION BY CONTINUOUS ANION EXCHANGE CHROMATOGRAPHY

[75] Inventors: Thomas S. Snyder, Oakmont; Harry M. Ferrari, Fox Chapel, both of Pa.

[73] Assignee: Westinghouse Electric Corp., Pittsburgh, Pa.

[21] Appl. No.: 620,807

[22] Filed: Dec. 3, 1990

[51] Int. Cl.$^5$ ............................................. B01D 5/00
[52] U.S. Cl. ................... 204/157.2; 204/157.21; 423/7; 210/657; 210/682
[58] Field of Search ............ 204/157.2, 157.21; 252/632; 210/657, 682; 423/6, 7, 2

[56] References Cited

U.S. PATENT DOCUMENTS

| | | | |
|---|---|---|---|
| 3,511,620 | 5/1970 | Shimokawa et al. | 423/7 |
| 3,869,536 | 7/1975 | James | 423/7 |
| 3,953,569 | 4/1976 | Seko et al. | 423/7 |
| 3,971,842 | 7/1976 | Ewbank | 423/7 |
| 4,112,044 | 9/1978 | Miyake et al. | 423/7 |
| 4,118,457 | 10/1978 | Seko et al. | 423/7 |
| 4,368,175 | 1/1983 | Miyake et al. | 423/7 |
| 4,490,225 | 12/1984 | Lahoda et al. | 204/158 R |
| 4,584,183 | 4/1986 | Chiang et al. | 423/2 |
| 4,748,008 | 5/1988 | Takeda et al. | 423/6 |
| 4,764,276 | 8/1988 | Berry et al. | 210/264 |
| 4,767,513 | 8/1988 | Peterson et al. | 204/157.21 |
| 4,803,057 | 2/1989 | Takeda et al. | 423/6 |
| 4,808,317 | 2/1989 | Berry et al. | 210/660 |
| 4,915,843 | 4/1990 | Taniguchi et al. | 210/635 |
| 5,023,061 | 6/1991 | Snyder et al. | 423/70 |

FOREIGN PATENT DOCUMENTS 786896 2/1955 United Kingdom.

OTHER PUBLICATIONS

Document dated Mar. 7, 1989 entitled "Multicomponent Separations by Continuous Annular Chromatography" (Industrial Liaison Group Meeting).

Primary Examiner—Brooks H. Hunt
Assistant Examiner—Ngoclan T. Mai

[57] ABSTRACT

A simple, low temperature process for separating uranium isotopes and producing substantially pure uranium isotope fractions from a crude uranium isotope-containing aqueous feed stock is provided. A uranium isotope-containing solution is fed to an anion exchange resin in a continuously rotating annular chromatograph as a suitable eluant is also simultaneously fed to the rotating chromatograph. A Uranium 235, a Uranium 238 and an impurity fraction are recovered from the chromatograph. The substantially pure uranium 235 and uranium 238 fractions may be subjected to further processing, preferably precipitation with ammonium hydroxide to produce ammonium diuranate, and then calcining to form uranium oxide rich in the desired isotope.

20 Claims, 3 Drawing Sheets

URANIUM ISOTOPE SEPARATION BY CONTINUOUS ANION EXCHANGE CHROMATOGRAPHY

TECHNICAL FIELD

The present invention relates generally to uranium isotope separation and purification processes and specifically to a simplified method of separating and purifying uranium isotopes by continuous annular chromatography.

BACKGROUND ART

Uranium constitutes about $8 \times 10^{31.5}\%$ of the igneous rocks in the earth's crust, primarily in the form of the ores uraninite ($UO_2$), pitchblende ($U_3O_8$) and carnotite ($2K(UO_2)UO_4 3H_2O$). The uranium 235 ($U^{235}$) isotope, which constitutes about 0.7% of natural uranium, has chemical properties identical to those of the more abundant uranium 238 ($U^{238}$) isotope. These naturally occurring uranium isotopes are the primary useful naturally occurring isotopes. $U^{235}$ is used mainly in nuclear applications, while $U^{238}$ is used in weapons and ordnance applications. However, before the isotopes can be used for these purposes, they must be separated.

Because of their identical chemical properties, it was thought that $U^{235}$ and $U^{238}$ could not be separated by chemical methods. Consequently, various nonchemical uranium isotope separation methods have historically been proposed. Methods proposed to separate uranium isotopes, specifically $U^{235}$ and $U^{238}$, have included thermal difussion employing molten uranium, gaseous diffusion through barriers, the centrifugation of gaseous uranium, and electromagnetic processes wherein $U^{235}$ ions were deflected more than $U^{238}$ ions in a magnetic field.

Uranium separation and enrichment processes, until recently, have been the province of various agencies of the United States government. One commonly used process involves the differential high temperature diffusion rates of the hexafluorides of the uranium isotopes $U^{235}F_6$ and $U^{238}F_6$, which have different difussion rates. A laser-driven enrichment process has also been used in the production of nuclear grade uranium.

Early workers tried to separate the isotopes of uranium by eluting the uranyl ion, $UO_2^{+2}$, on cation-exchange resin with various eluant ions. While some minor separations were achieved, the separation factor was too low to be practicable. Larger separation factors were obtained by passing uranyl ions over resin in the uranous ion form.

When an aqueous solution of uranyl chloride encounters a cation exchange bed containing uranous ion, the cation exchange equilibria tend to favor the concentration of the $U^{238}$ isotope as sorbed tetravalent uranous ions on the cation exchange bed and to favor enrichment of the $U^{235}$ isotope in the aqueous solution of hexavalent uranyl ions. A variety of procedures has been proposed relating to uranium enrichment using a cascade of a great many ion exchange beds because the maximum separation factor per theoretical stage (that length of bed required to establish the equilibrium isotopic partition) is only about 1.0007. None of these numerous proposals, however, was sufficiently attractive to be commercialized.

While the aforementioned processes ultimately accomplish the desired separation and enrichment of the uranium isotopes needed for nuclear applications, they do so at high processing cost. In addition, since the methods currently used to separate uranium isotopes are primarily enrichment processes and do not also purify the uranium, the uranium-containing material to be processed requires extensive preparation to achieve the purity necessary for nuclear grade uranium 235. Uranium 238 does not have to meet the same purity standards as $U^{235}$. Both the diffusion cascade process and the centrifugation process now in use have very high energy requirements since both employ high temperature, vapor phase operations to enrich the $U^{235}$ isotopes produced. Moreover, the size of the equipment needed to conduct these processes is extremely large, and a very large facility is required to hold this equipment. Finally, the end product of the aforementioned processes is only an enriched and not an isotopically pure product.

U.S. Pat. No. 3,869,536 to James discloses a chromatographic uranium enrichment process wherein a composition having an isotopic distribution of $U^{235}$ and $U^{238}$ which is different from the uranium isotope distribution of the feed stock is prepared. The uranous-uranyl chromatographic displacement method described therein employs a cation exchange bed requiring a shorter length of each theoretical stage of enrichment than was previously necessary. A series of interconnected columns through which liquid flows downwardly from one column to another to effect the change in isotopic distribution is described for use with this process. Although the James process produces changes in the uranium isotope distribution of the uranium-containing feed stock, there is no suggestion that the production of nuclear fuel quality pure $U^{235}$ is an objective. Moreover, the process requires several reaction vessels.

U.S. Pat. No. 3,971,842 to Eubank discloses a process for the separation and enrichment of uranium isotopes which includes a cascade of ion exchange units designed to produce fuel grade uranium. This process, like that of James, employs a cation exchange bed, but one which may move relative to its chamber. In certain embodiments, the ion exchange bed has an annular shape so that the relative movement between the bed and its chamber is achieved by rotation of the annular bed about the axis. A uranium solution is fed to the bed and subjected to oxidation and reduction along sequential regions in the bed so that solutions of uranium withdrawn from the uranium area of the bed have an isotopic uranium distribution different from the uranium feed. In addition, solutions may enter and leave from the sidewalls of the ion exchange bed. The relative movement between the ion exchange bed and chamber column assists in the enrichment of the uranium ions, which occurs as a result of exchange between the aqueous solution and hexavalent uranium and sorbed tetravalent uranium.

The method and system disclosed in U.S. Pat. No. 3,971,842 represents an effective way to separate uranium isotopes and to enrich the $U^{235}$ isotope fraction. However, this method requires both complex, bulky equipment and many involved process steps. In addition, the Eubank method is primarily a uranium enrichment process and does not guarantee the production of isotopically pure $U^{235}$ suitable for use as nuclear fuel. The many stages and different processing chemicals required to produce $U^{235}$ according to this method, moreover, add substantially to the processing cost.

The prior art discloses a multitude of systems and methods for separating various chemical species, including isotopes. U.S. Pat. Nos. 4,490,225 to Lahoda et al. and 4,584,183 to Chiang et al., for example, are directed to the separation of zirconium isotopes. U.S. Pat. No. 4,584,183 discloses the enrichment of a zirconium isotope component of an aqueous solution by a solvent extraction-exchange process that includes an organic phase, while U.S. Pat. No. 4,490,225 uses a laser to irradiate the vapor of a zirconium-containing compound to separate the isotopes. The processes described in these patents, however, are not suggested to be applicable to the separation of any isotopes other than those of zirconium.

U.S. Pat. Nos. 4,764,276 and 4,808,317 to Berry et al. disclose apparatus useful for separating components in liquid solution. A rotating separator body including discreet chambers of ion exchange resin allows the continuous processing of a liquid feed solution. Although the apparatus described in these patents allows an ion exchange type of separation process to be conducted continuously in a single reaction vessel, there is no suggestion whatever in either patent that the purification or separation of uranium isotopes could be conducted according to the processes described therein.

British Patent No. 786,896 also described a continuous separation process for the chromatographic separation of mixtures with two or more components. The mixture is added to a separating medium, such as an ion exchange resin, and the separating medium is moved relative to the added mixture. An elution agent is passed continuously through the medium, and the separated components are continuously collected. However, there is no teaching that the separation and purification of uranium isotopes can be accomplished according to this process.

The prior art, therefore, has failed to provide a simple, low cost method for efficiently and effectively separating and purifying uranium isotopes, which produces uranium 235 of a quality suitable for nuclear applications.

SUMMARY OF THE INVENTION

It is a primary object of the present invention, therefore, to overcome the disadvantages of the prior art and to provide an efficient, simple and low cost method to separate and purify uranium isotopes.

It is another object of the present invention to provide a method for the separation and purification of isotopes that may be conducted continuously in uranium isotopes that may be conducted continuously in a single separations vessel at lower process temperatures than prior art processes.

It is still another object to provide a method for the separation and purification of uranium isotopes that produces substantially pure $U^{235}$ suitable for nuclear applications.

It is a still further object of the present invention to provide a uranium isotope separation and purification process which accepts a crude, low purity uranium feed stock and produces substantially pure, highly enriched $U^{235}$.

It is yet a further object of the present invention to provide a method for separating and recovering a substantially pure $U^{235}$ isotope fraction and a substantially pure $U^{238}$ isotope fraction from a uranyl sulfate feed stock using one of several separation chemistries.

It is yet another object of the present invention to provide a continuous chromatographic process which employs an anion exchange resin bed and uses an isocratic, gradient or displacement elution mode.

The aforesaid objects are achieved by providing a continuous process which both separates and chemically purifies uranium 235 and uranium 238 isotopes in a single separations vessel. High pressure liquid ion exchange chromatography is employed in a separation system wherein the stationary phase, the mobile phase, and the elution mode are controlled to optimize the isotopic separation. The preferred separation systems use sulfates or chlorides as the mobile phase, although nitrates and carbonates can also be used. A continuous rotating annular chromatograph employing an anion exchange or chelating resin stationary phase simultaneously separates a $U^{235}$ fraction from a $U^{238}$ fraction and from an impurity fraction. Each uranium isotope fraction is precipitated with ammonium hydroxide to form ammonium diurante and then calcined to produce uranium oxide rich in either $U^{238}$ for ordnance applications or $U^{235}$ for nuclear fuel applications.

Other objects and advantages will be apparent from the following description, claims and drawings.

DESCRIPTION OF THE PREFERRED EMBODIMENTS

Because the available uranium isotope separation processes are essentially enrichment rather than purification processes, a uranium feed stock that has been subjected to at least some degree of purification is required for these processes. Moreover, the prior art processes require large, costly equipment, and those that operate at high temperatures have high energy requirements. As a result, until the present invention, the separation of substantially pure nuclear fuel quality $U^{235}$ has only been effectively achieved when facilities capable of purifying the uranium-containing feed stock and then subjecting this stock to the complex series of process steps required to separate the uranium 235 from $U^{238}$ and other isotopes were available. The present invention has greatly simplified the uranium isotope separation process to produce substantially pure isotope fractions at costs significantly lower than those of prior art uranium isotope separation processes.

Figure 1:
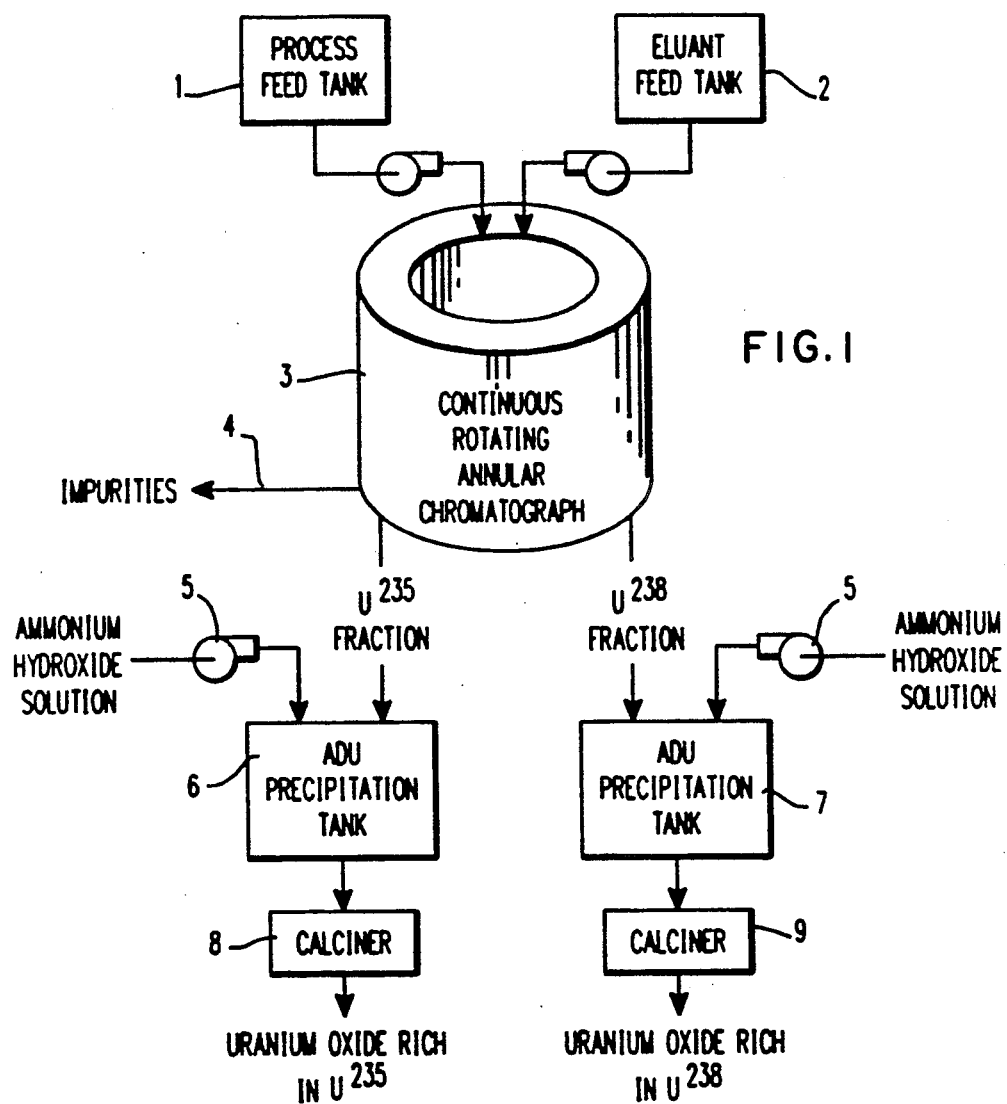
FIG. 1 illustrates schematically the process of the present invention.

FIG. 1 illustrates schematically the uranium isotope separation process of the present invention. A solution containing the uranium isotopes to be separated and a suitable eluant are fed to a continuous rotating annular chromatograph containing an anion exchange bed in a manner to be described in detail hereinbelow. A uranium 235 ($U^{235}$) isotope fraction is chromatographically separated from a uranium 238 ($U^{238}$) isotope fraction and from an impurity fraction in the rotating annular chromatograph, and these fractions are collected. Ammonium hydroxide is added to each of the uranium isotope fractions and precipitated as ammonium diuranate (ADU). The ADU precipitated from the $U^{235}$ fraction is calcined to produce uranium oxide rich in $U^{235}$, and the ADU precipitated from the $U^{238}$ fraction is calcined to produce uranium oxide rich in $U^{238}$.

The uranium separation process of the present invention exhibits greatly improved separation efficiency over prior art processes. This high pressure, liquid anion exchange chromatographic separation process employs several separation process mechanisms simultaneously. A mobile phase, which includes the eluant selected to effect the isotopic separation, is used in connection with a stationary phase in the annular chromatograph. The overall uranium isotope separation mechanism may be influenced by several transport processes in the mobile phase, which are illustrated schematically in FIG. 2 and labeled as a, b, c, d and e. The solution containing the mixture of uranium isotopes to be separated is passed through the stationary phase, which includes a bed of ion exchange beads in the continuous rotating annular chromatograph used in this process. The different uranium isotopes are transported at different rates through the ion exchange beads and differ in their interaction with the ion exchange material. Uranium 238 is slightly larger and heavier than Uranium 235 and will, therefore, behave somewhat differently than Uranium 235.

Figure 2:
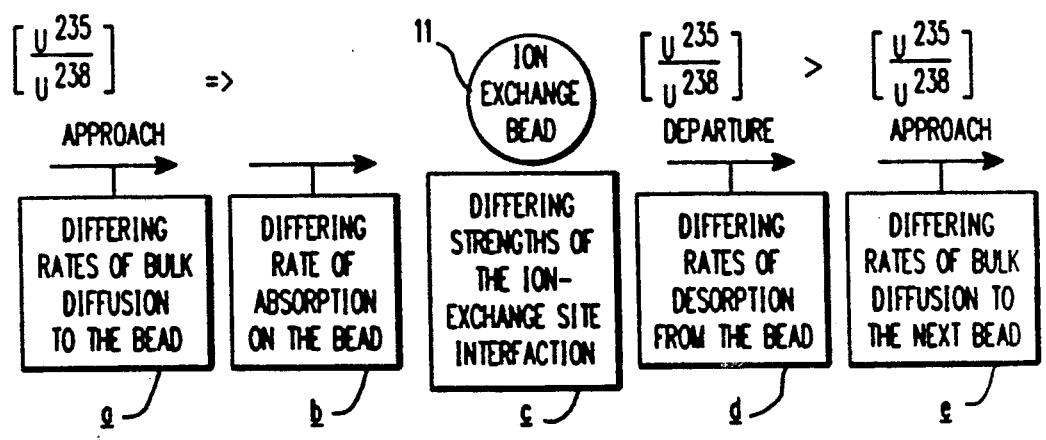
FIG. 2 is a schematic representation of the ion exchange chromatography process of the present invention.

Referring to FIG. 2, as the $U^{235}$ and $U^{238}$ isotopes approach an ion exchange bead (Process a), the rates of bulk diffusion differs. Once the isotopes reach the bead, the rates of adsorption on the bead differ (Process b) for each of these isotopes. In addition, the strength of the interaction of the ion exchange site with the uranium isotope (Process c) is different for $U^{235}$ and for $U^{238}$. After the ion exchange reaction has occurred, the isotopes are desorbed from the ion exchange bead (Process d) and then diffuse in bulk to the next bead (Process e). $U^{235}$ will be desorbed from the bead and diffuse to the next bead at a different rate than will $U^{238}$.

The overall uranium isotope separation process may also be influenced by the characteristics of the stationary phase used in conjunction with the present process. By carefully tailoring the characteristics of the stationary phase, the length of a theoretical stage in the separation process can be reduced, which leads to a substantial reduction in both the size and cost of the separation equipment. The combination of the uranium isotope-containing solution transport rate through the ion exchange medium and the stationary phase effects increases uranium isotope separation efficiency. This allows both uranium isotope separation and impurity removal in the same process vessel.

In addition to the effects on the separation process created by the transport processes and the stationary phase characteristics, the elution mode must also be controlled to optimize isotopic separation. Various different elution modes, such as isocratic, gradient, displacement and the like, can be employed with this process, depending on the separation chemistry selected to achieve the desired isotopic separation.

Figure 3:
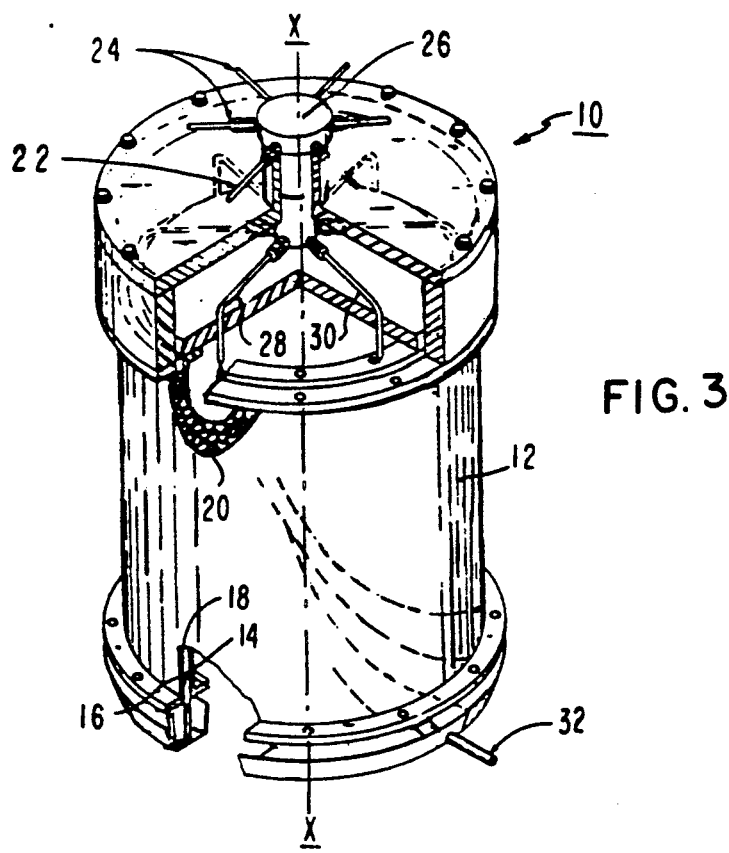
FIG. 3 illustrates one embodiment of a rotating annular chromatograph that can be used in the process of the present invention.
Figure 4:
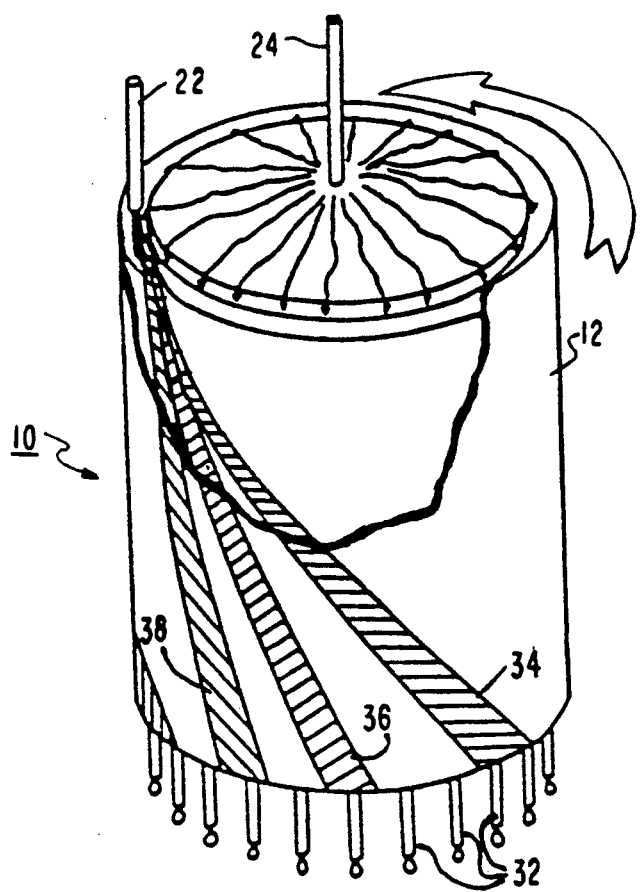
FIG. 4 is a diagrammatic representation of the separation of the isotopic feed components produced by the annular rotating chromatograph of FIG. 3.

One type of the continuous rotating annular chromatograph which forms the single separation vessel preferred for the present process is shown in FIGS. 3 and 4. The continuous annular chromatograph especially preferred for the uranium isotope separation process described herein was developed by Oak Ridge National Laboratory. This type of chromatograph 10 includes an annulus 12 which contains the stationary phase of the system. The annulus 12 rotates about a central axis x during operation. The annulus includes an inner cylinder 14 and a concentric outer cylinder 16. The inner cylinder 14 has a smaller diameter than the outer cylinder, which forms a packing space 18 between the two cylinders. The packing space 18 contains the stationary phase of the separation system, which may be a bed of ion exchange beads, such as the beads 20 shown in FIG. 3, or any other suitable stationary phase material that can be used to effect the desired uranium isotope separation.

A feed inlet 22 directs the uranium isotope-containing feed stock into the chromatograph. One or more eluant inlets 24 are preferably angularly offset from the feed inlet 22. A stationary inlet distributor 26 directs the feed and the eluant to feed nozzles and eluant nozzles, respectively. Only a single feed nozzle 28 and eluant nozzle 30 are shown in FIG. 3. One or more product collection outlets 32 is provided to collect the liquid fractions separated by the process. The positions of the product collection outlets are set to accommodate the particular operating conditions set for the process. Each product collection outlet 32 collects an elution volume which has had a particular residence time in the chromatograph. The annulus 12 containing the stationary phase 20 is typically rotated at a constant speed so that any vertical segment of the annulus is above a particular fixed product collection outlet at a given time after this segment has been loaded with uranium isotope-containing feed stock and eluant. Consequently, each product collection outlet has an angular position which corresponds to a particular elution time for a particular rate of rotation of the stationary phase and for a particular flow rate through the stationary phase.

The flow rate of the uranium-containing feed stock and the eluant through the stationary phase is controlled by both the pressure drop across the effective height of the stationary phase and the physical characteristics of the stationary phase, i.e., particle size and packing void volume. This pressure drop may be provided by the hydrostatic head of the feed stock and eluant, but it is preferably provided by pressurizing the chromatograph. The pressure required to achieve a particular flow rate is governed by the nature of the stationary phase (i.e., packing, average particle size and particle size distribution). The smaller the average particle size of the beads making up the stationary phase, the larger the pressure drop that is required to obtain a particular flow rate over a particular effective height. However, the separation factor for any given theoretical stage is improved as the average particle size of the ion exchange beads is decreased. Thus, the effective height needed to effect a given degree of separation is decreased as the separation capacity of a unit length (or theoretical stage height) is increased by decreasing the average particle size of the beads. The flow rate across the effective height of the stationary phase and the rotational speed of the stationary phase should be coordinated so that a particular product fraction always elutes at the same angular position and thus is always delivered to the same product collection port.

The angular displacement between the feed inlet 22 and the eluant inlet 24 and the speed of rotation of the annulus 12 containing the ion exchange beads 20 is selected so that the time interval between loading and elution is just sufficient for the desired degree of penetration. The relationship between the time for loading and the depth of penetration of the stationary phase by the feed stock and eluant is governed by the flow rate through the ion exchange bed formed by the ion exchange beads 20 in the packing space 18 in the annulus 12. The displacement may be affected by either an isocratic or a gradient supply of eluant. In the former case, the eluant can simply be supplied from a single eluant inlet while in the latter case, several eluant inlets at successively greater angular displacements from the feed inlet are utilized.

Decreasing the elution volumes by gradient elution or by other means increases the concentration of the desired product, i.e., the specific uranium isotope to be separated, in the product fraction. Concentrations greater than about 5 g/l, especially between about 20 and 70 g/l are preferred. Maximizing the concentration of product reduces the total volume of fluid to be processed. This allows a reduction in the overall size of the system with a consequent reduction in capital and operating expenses. However, practical considerations, such as solubility limits, may constrain the maximum concentrations obtainable.

The flow rate down the annulus 12, which functions as the chromatographic column in this case, is governed by the pressure drop from the top to the bottom of the annulus 12 and by the nature of the stationary phase. The smaller the average particle size of the ion exchange beads making up the stationary phase, the higher the pressure drop that is required to obtain a given flow rate. This relationship is also affected by the particle size distribution of these resin beads. There is, however, a maximum attainable flow rate for any given ion exchange resin stationary phase which cannot be exceeded by the application of additional pressure. The suppliers of such resins rate them in terms of flow rate per given pressure drop and maximum attainable flow rate.

It is preferred to use a stationary phase which will permit flow rates between about 2 and 80, more preferably between about 3 and 20 gallons per minute per square foot of cross sectional area (between about $1.36 \times 10^{-3}$ and $5.43 \times 10^{-2}$ m$^3$/sec, more preferably between about $2.04 \times 10^{-3}$ and $1.36 \times 10^{-2}$ m$^3$/sec per square meter of cross sectional area). There is a relationship between the achievable flow rates and the effective column height needed for a given degree of purity. For a given system of stationary phase and eluant, the theoretical stage separation factor, $\alpha_s$, of the stationary phase will increase as the average particle size of the ion exchange beads of the stationary phase decrease. However, as this particle size decreases so does the flow capacity of the stationary phase. Thus, there is an inverse relationship between $\alpha_s$ and the flow capacity. Thus, a higher flow rate will require a greater effective column height to achieve the same degree of separation or product fraction purity.

Furthermore, there is the additional constraint that the pressure required to achieve the desired flow rate should not exceed the capability of available pumps, seals or feed tubing. The required pressure is a function of both the pressure drop needed per unit of effective height and the total effective height required for the desired degree of separation. Thus, as the flow capacity of the stationary phase is increased by a change in its physical configuration and consequently its theoretical stage separation factor, $\alpha_s$, the required overall pressure drop are both increased. On the other hand, as the theoretical stage separation factor, $\alpha_s$, is increased by a change in the resin bead size distribution and consequently the flow capacity of the stationary phase is decreased, the pressure drop for a given effective height is increased. A pressure drop of less than about 2758 kPa (400 psi) more especially between about 345 and 1042 kPa (50 and 150 psi) is preferred.

To obtain a system with a commercially practical capacity, therefore, it is necessary to use a stationary phase which will simultaneously display both a reasonable theoretical stage factor, $\alpha_s$, and a reasonable flow rate per unit of effective height with a reasonable pressure drop. This can be achieved by an appropriate selection of both the ionic capacity of the stationary phase ion exchange resin and the eluant.

Several product collection outlets 32 may be used to collect a particular product fraction. This is accomplished by closely spacing these collection outlets, as shown in FIG. 4, so that they more than span the angular range of rotation that corresponds to the elution time interval of that particular fraction, but do not extend to angular positions at which any significant portion of any other product fraction is expected to elute. Of course, this requires that the elution time intervals of different product fractions do not substantially overlap. This arrangement tends to insure that minor fluctuations in the steady state elution behavior which would cause a slight advancement or retardation of the elution time of the desired product fraction will not result in any loss of this fraction.

The continuous annular chromatograph 10 shown in FIGS. 3 and 4 can be used to practice the process of the present invention in a manner that fulfills these requirements.

Isotopic separation of $U^{235}$ and $U^{238}$ according to the present process is sharpened further by tailoring the physical characteristics of the stationary phase. The stationary phase or ion exchange material that is most effective in separating uranium isotopes according to the present process preferably has spherical shape particles, a monodisperse particle size distribution and a particle size less than 100 microns. The preferred ideal ion exchange particle size would be 0.1 to 1.0 microns or smaller. However, the reality of operation requires preferred particle sizes of up to 50 microns and larger. When these stationary phase characteristics are carefully selected, the length of a theoretical stage and, hence, the size and cost of the uranium isotope separation equipment are reduced as size decreases. Moreover, uranium isotope separation efficiency is increased by the effect of the stationary phase characteristics in combination with the combined transport rates discussed above so that the uranium isotopes can be separated and the impurities removed entirely within the single continuous annular chromatograph 10. Additional processing equipment is not required.

Uranium forms a number of anionic complexes, including sulfate, chloride, nitrate and carbonate. Consequently, the stationary phase selected for the separation process may take advantage of different exchange groups, provided that the stationary exchange group selected is compatible with both the feed and mobile phase chemistries used to effect the separation. Table I lists some suitable stationary phase materials known to interact with anionic uranium complexes.

TABLE I

| Resin | Manufacturer | Total Capacity | |
|---|---|---|---|
| | | Milli-equivalents per gram | Milli-equivalents per milliliter |
| Amberlite IRA-400 | Rohm & Haas Co. | 3.9 | 1.2 |
| Amberlite IRA-405 | Rohm & Haas Co. | — | 1.6 |
| Amberlite IRA-425[a] | Rohm & Haas Co. | — | 1.3 |
| Dowex 1 | Dow Chemical Co. | 3.5 | 1.33 |
| Dowex 11 | Dow Chemical Co. | 4.0 | 1.24 |
| Dowex 21K[a] | Dow Chemical Co. | 4.5 | 1.25 |
| Duolite A-101D | Diamond Alkali Co. | 4.2 | 1.4 |
| Nalcite | [b] | — | — |
| Ionac A-580 | Ionac Chemical Co. | — | (min.) 1.30 |
| Ionac A-590[a] | Ionac Chemical Co. | — | (min.) 1.30 |
| Permutit SK | [c] | 4.3 | 1.40 |
| Permutit SKB[a] | [d] | — | — |

[a]Available as coarse-bead product for use in resin-in-pulp circuits.
[b]Dowex resins marketed by Nalco Chemical Company.
[c]Same as Ionac A-580.
[d]Same as Ionac A-590.

In addition to those resins listed in Table I, any of the chelating resins which interact with anionic uranium complexes may also be used as the stationary phase in the present process.

Figure 5:
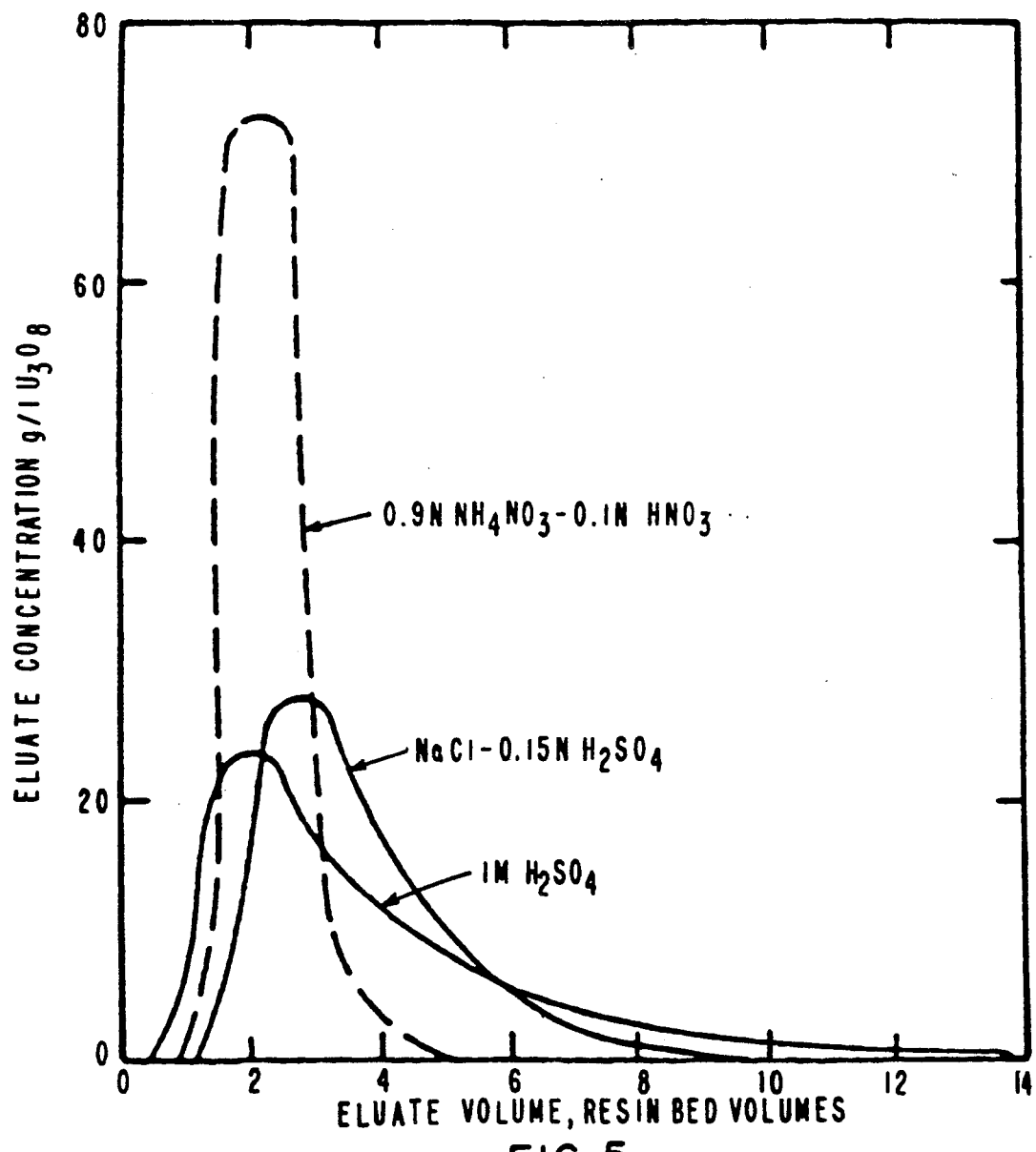
FIG. 5 represents graphically elution curves for $U_3O_8$ in various solutions.

Optimization of the mobile phase is based on the elution characteristics of the various acids used for this purpose and also on the composition of the feed uranium solute species. FIG. 5 illustrates the use of sulfate and nitrate solutions to elute uranium-loaded resins containing $U_3O_8$ and the resulting elution curves. Chloride solutions that are about 0.5 to 1.5 molar in $Cl^-$ have also been found to be effective eluants. In fact, it has been discovered that an eluant with a concentration of about 3 to 6 molar chloride increases the interaction of the solute with the ion exchange material and, as a result, may improve the isotopic separation efficiency.

The following Examples describe two preferred embodiments of the present process. The process conducted is outlined schematically in FIG. 1.

EXAMPLE 1

1.0M uranyl sulfate in aqueous solution is the uranium-containing feed stock. Because the present process both eliminates impurities and separates isotopes, the chemical purity of the feed stock can vary. The 1.0M uranyl sulfate is added to the process feed tank, from which it is supplied to the continuous rotating annular chromatograph 10 at a rate that loads preferably less than 10% of the active chromatographic length of the chromatograph as the stationary phase 20 rotates under the fixed feed inlet 22. The stationary phase 20 is an anion exchange resin, preferably Amberlite IRA-400 or, alternatively, Dowex 21 with spherical morphology and an average particle size less than 1.0 micron. The eluant feed tank is loaded with 1 to 4 molar aqueous $H_2SO_4$ solution. Either an isocratic or a gradient elution mode can be used to direct the mobile phase eluant through the stationary phase. The eluant is injected along the remainder of the circumference of the chromatograph. The chromatograph is pressurized as described above and rotated to separate the uranium isotope fractions in the feed stock.

At least three product fractions are recovered as a function of their circumferential displacement around the chromatograph following elution. The circumferential displacement of the product fractions is illustrated in FIG. 4. Product fraction 34 represents the impurities in the uranyl sulfate feed stock which are removed through the product collection outlets 32 under this fraction and disposed of. Product fraction 36 is an enriched $U^{235}$ fraction. This is removed from the chromatograph, precipitated as ammonium diuranate (ADU), calcined to uranium oxide and then further processed into nuclear fuel assemblies. Product fraction 38 is the fraction of the uranyl sulfate feed depleted of both impurities and $U^{235}$. This fraction is rich in $U^{238}$ and may be processed as shown in FIG. 1 to $U^{238}$ oxide and further processed as necessary for ordnance and weapons applications where explosive grades of uranium are desired.

Tables II and III below illustrate, respectively, the effects of the concentrations of uranium and sulfate on resin loading.

TABLE II

Effect of Concentration of Uranium in Solution on Resin Loading
Conditions: 5.0 g $H_2SO_4$/liter, 30.0 g $SO_4$/liter total with excess sulfate added as $MgSO_4$, Amberlite IRA-400 resin.

| g $U_3O_8$/liter | Uranium loading lb $U_3O_8$/cu ft |
|---|---|
| 0.22 | 2.90 |
| 0.59 | 3.70 |
| 1.18 | 4.42 |
| 2.95 | 5.54 |

TABLE III

Effect of Concentration of Total Sulfate on Uranium Loading of Resin
Conditions: 1.18 g $U_3O_8$/liter, 5.0 g $H_2SO_8$/liter with excess sulfate added as $MgSO_4$, Amberlite IRA-400 resin.

| g $SO_4$/liter | Uranium loading lb $U_3O_8$/cu ft |
|---|---|
| 20 | 4.50 |
| 30 | 4.42 |
| 50 | 4.21 |

EXAMPLE 2

The process of Example 1 is conducted with the same uranyl sulfate feed stock and anion exchange resin stationary phase. However, the mobile phase eluant is 0.5 to 6M aqueous hydrochloric acid, so that chloride separation chemistries are employed. A gradient elution mode is also preferred. The same product fractions are produced with the chloride system as with the sulfate system so that substantially pure $U^{235}$ may be obtained from a crude uranium-containing feed stock.

Nitrate and carbonate separation chemistries can also be used to effect the uranium 235 and uranium 238 separations produced by the sulfate and chloride systems described above. Like the sulfate and chloride systems, these separation chemistries both purify and separate the uranium isotopic fractions so that a nuclear grade purity uranium feed stock is not required. Consequently, significant processing economies can be achieved. Additionally, substantially pure uranium isotopes can be produced with any of these separation chemistries.

INDUSTRIAL APPLICABILITY

The process of the present invention will find its primary applicability in uranium processing facilities or wherever the production of substantially pure uranium isotope fractions from a crude uranium-containing feed stock is desired. The process described herein is especially suitable for producing nuclear quality uranium 235.

We claim:

1. A process for producing a substantially pure uranium isotope fraction from an aqueous feed stock containing a mixture of uranium isotopes and impurities, said process including:
   (a) introducing said aqueous feed stock at a first, fixed point at the top of a resin medium in a rotating annular chromatograph;
   (b) introducing an eluant at a second point at the top of said resin medium angularly displaced from said first point;
   (c) continuously rotating said annular chromatograph during steps (a) and (b) while said chromatograph is pressurized to cause the isotopes said uranium isotope-eluant to be circumferentially displaced as said feed stock and said eluant travel from the top to the bottom of the chromatograph to produce a substantially pure product fraction corresponding to each uranium isotope desired to be separated from said feed stock and an impurity fraction; and
   (d) collecting each said substantially pure uranium isotope product fraction and said impurity fraction.

2. The process described in claim 1, wherein said feed stock includes the uranium isotopes $U^{235}$ and $U^{238}$.

3. The process described in claim 2, wherein said feed stock is an aqueous solution of uranyl sulfate.

4. The process described in claim 3, wherein said resin medium is selected from the group consisting of anion exchange resins and chelating resins.

5. The process described in claim 4, wherein said resin medium is an anion exchange resin.

6. The process described in claim 4, wherein said resin medium is a chelating resin.

7. The process described in claim 5, wherein said eluant is selected from the group consisting of aqueous solutions of sulfates, chlorides, nitrates and carbonates.

8. The process described in claim 7, wherein said eluant is $H_2SO_4$.

9. The process described in claim 7, wherein said eluant is HCl.

10. The process described in claim 7, wherein said eluant is $HNO_3$.

11. The process described in claim 1, wherein said feed stock includes an anionic uranium complex, said resin medium is an anion exchange resin, and said eluant is selected from the group consisting of aqueous solutions of sulfates and chlorides.

12. The process described in claim 11, wherein said anion exchange resin comprises spherical particles of said resin less than 100 microns in size.

13. The process described in claim 1, further including the steps of, after step (d), precipitating said substantially pure uranium isotope product fraction with ammonium hydroxide to produce ammonium diuranate and calcining said ammonium diuranate to produce uranium oxide rich in said uranium isotope.

14. A process for producing nuclear quality Uranium 235 ($U^{235}$) from a substantially impure feed stock containing a mixture of uranium isotopes, including $U^{235}$, including the steps of:
   (a) forming a stationary phase from an anion exchange resin in the annulus of a rotating annular chromatograph;
   (b) feeding said feed stock to said stationary phase to load less than 10% of said stationary phase;
   (c) injecting a mobile phase comprising an eluant selected from the group consisting of aqueous solutions of sulfates, chlorides, nitrates and carbonates into said stationary phase;
   (d) continuously rotating said annular chromatograph during steps (b) and (c) while said chromatograph is pressurized to cause said feed stock and said mobile phase to move downwardly through said stationary phase so that said $U^{235}$ isotopes are separated from other uranium isotopes in said mixture and from said impurities;
   (e) collecting said $U^{235}$ isotope in substantially pure, enriched form from said stationary phase;
   (f) precipitating said $U^{235}$ isotope as ammonium diurante with ammonium hydroxide; and
   (g) calcining said ammonium diuranate to produce uranium oxide rich in $U^{235}$ suitable for nuclear applications requiring substantially pure $U^{235}$.

15. The process described in claim 14, wherein said feed stock is uranyl sulfate and said eluant is an aqueous solution of a sulfate.

16. The process described in claim 15, wherein said feed stock is 1.0 molar uranyl sulfate and said eluant is 1 to 4 molar $H_2SO_4$.

17. The process described in claim 16, wherein said stationary phase comprises an anion exchange resin with spherical morphology and an average particle size less than 100 microns.

18. The process described in claim 17, wherein said mobile phase is injected into said stationary phase in an elution mode selected from the group consisting of isocratic and gradient elution modes.

19. The process described in claim 14, wherein said feed stock is 1.0 molar uranyl sulfate and said eluant is 0.5 to 6.0 molar HCl.

20. The process described in claim 19, wherein said mobile phase is injected into said stationary phase in a gradient elution mode.

* * * * *